United States Patent [19]

Miller et al.

[11] Patent Number: 4,507,399
[45] Date of Patent: Mar. 26, 1985

[54] CADMIUM-CONTAINING CATALYST

[75] Inventors: Jeffrey T. Miller; Thomas D. Nevitt, both of Naperville, Ill.

[73] Assignee: Standard Oil Company (Indiana), Chicago, Ill.

[21] Appl. No.: 536,673

[22] Filed: Sep. 28, 1983

[51] Int. Cl.³ .......................... B01J 21/16; B01J 23/06
[52] U.S. Cl. .......................................... 502/63; 502/84
[58] Field of Search ................. 502/64, 68, 84, 202, 502/253, 63

[56] References Cited

U.S. PATENT DOCUMENTS

| | | |
|---|---|---|
| 2,301,735 | 11/1942 | Melaven et al. ............... 502/253 X |
| 3,328,119 | 6/1967 | Robson ............................ 502/64 X |
| 3,472,860 | 10/1969 | Hargrave ....................... 502/253 X |
| 3,507,812 | 4/1970 | Smith et al. .................... 502/68 X |
| 4,176,090 | 11/1979 | Vaughan et al. ............... 502/84 X |
| 4,269,813 | 5/1981 | Klotz .............................. 502/202 X |
| 4,384,155 | 5/1983 | Chu ................................. 585/466 |

*Primary Examiner*—Carl F. Dees
*Attorney, Agent, or Firm*—James R. Henes; William T. McClain; William H. Magidson

[57] ABSTRACT

A catalyst composition comprising a cadmium component and a support comprising at least one of a crystalline borosilicate and a pillared smectite or vermiculite clay is disclosed.

7 Claims, No Drawings

CADMIUM-CONTAINING CATALYST

BACKGROUND OF THE INVENTION

1. Field of the Invention

This invention relates generally to a cadmium-containing catalyst and more particularly concerns such catalyst for the reaction between hydrogen and a material selected from the group consisting of (a) carbon monoxide, (b) at least one of an an alcohol containing from 1 to 6 carbon atoms and an olefin containing from 2 to 6 carbon atoms, (c) a mixture of an aromatic compound and at least one of carbon monoxide and an alcohol containing from 1 to 6 carbon atoms.

2. Description of the Prior Art

The production from less valuable materials of aliphatic compounds boiling in the gasoline range, of aromatic compounds, and of intermediates useful for the production of such aliphatic and aromatic compounds, is highly desirable and has been the object of several prior art methods involving the use of cadmium-containing catalysts. For example, Woodruff et al., U.S. Pat. Nos. 1,625,924 and 1,625,928, disclose a method for producing methanol by reacting oxides of carbon with hydrogen at high pressures and in the presence of a catalyst comprising one or more non-reducible metal oxides, such as zinc, magnesium, cadmium, chromium, vanadium, or tungsten, and one or more easily reducible metal oxides, such as coppr, silver, iron, nickel, or cobalt, and a metallic halide. Melaven et al., U.S. Pat. No. 2,301,735, disclose a process for converting heavy hydrocarbon oils into gasoline by contacting the heavy oils with a catalyst comprising silica impregnated with a cadmium compound.

Klotz, U.S. Pat. No. 4,269,813, discloses a crystalline borosilicate catalyst comprising a molecular sieve material having the following composition in terms of mole ratios of oxides:

$$0.9 +/- 0.2 M_{2/n}O:B_2O_3:ySiO_2:zH_2O$$

wherein M is at least one cation, n is the valence of the cation, y is a value within the range of 4 to about 600, and z is a value within the range of 0 to about 160, and providing a specific X-ray defraction pattern. M represents an alkali metal cation, an alkaline earth metal cation, an ammonium cation, an alkylammonium cation, a hydrogen cation, a catalytically active metal cation, or mixtures thereof. Klotz also discloses that the original cation "M" in the above formulation can be replaced by tetraalkylammonium cations, metal ions, ammonium ions, hydrogen ions, and mixtures thereof, particularly hydrogen, rare earth metals, aluminum, metals of Groups IB, IIB and VIII of the Periodic Table, noble metals, manganese, and other catalytically-active materials and metals known to the art. The catalytically-active components can be present at concentrations from about 0.05 to about 25 weight percent of the crystalline borosilicate. Klotz discloses that the crystalline borosilicate can be employed effectively as a catalyst for various processes including reforming, hydrocracking, transalkylation, disproportionation, isomerization, and alkylation, and is particularly suitable for the isomerization of xylenes, the conversion of ethylbenzene and the conversion of alcohols, such as methanol, to useful products, such as aromatics or olefins.

Fraenkel et al., U.S. Pat. No. 4,294,725, disclose a Fischer-Tropsch catalyst comprising a particulate synthetic zeolite incorporating a transition metal reduced in situ by a preselected vaporous reductant metal and a method of making the catalyst. In the disclosed method for making the catalyst, at least one reducible transition metal is incorporated by ion exchange into a particulate synthetic zeolite catalyst support having ion-exchange properties, and the transition metal is then reduced with a vapor of at least one reductant metal having a reduction potential greater than the reduction potential of the transition metal. In one specific embodiment disclosed, cadmium is disclosed as a reducing metal which is present along with a transition metal in the final catalyst produced. Depending upon the conditions employed, saturated and unsaturated hydrocarbon products containing from one to five carbon atoms and an unidentified oxygenated product were produced when a catalyst containing cobalt as the transition metal and cadmium as the reducing metal was employed.

Chu, U.S. Pat. No. 4,384,155, discloses a process for the conversion of aromatic compounds, either alone or in admixture with a suitable alkylating agent, such as methanol or ethylene, to dialkylbenzene compounds which are rich in the 1,4-dialkylbenzene isomer, in the presence of a particular type of zeolite catalyst having a silica-to-alumina mole ratio of at least 12 and a constraint index of about 1-12, and containing a minor proportion of cadmium deposited thereon.

In addition, cadmium-containing catalysts have been employed in other unrelated methods. For example, Wietzel et al., U.S. Pat. No. 1,562,480, disclose a method for synthesizing higher molecular weight organic compounds containing oxygen by reacting an aliphatic alcohol with carbon monoxide and optionally with hydrogen at a temperature of at least about 400° C. and in the presence of the catalyst comprising both hydrogenating and hydrating constituents. Suitable hydrogenating constituents are disclosed as including copper, silver, gold, tin, lead, antimony, bismuth, zinc, cadmium and thallium, and suitable hydrating constituents are disclosed as including titanium, zirconium, thorium, vanadium, niobium, manganese, cerium, lanthanum, tantalum, chromium, molybdenum, tungsten, uranium, didymium, glucinium and aluminum.

Perkins et al., U.S. Pat. No. 2,107,710, disclose a method for hydrolyzing a halohydrocarbon in the vapor phase and in the presence of a catalyst comprising silica gell impregnated with one or more salts of metals belonging to the Groups IIB, IIIB, IVA or B, or VB of the periodic system, for example, beryllium nitrate, magnesium sulfate, zinc sulfate, cadmium nitrate, boron fluoride, aluminum chloride, stannous chloride, lead nitrate, titanium tetrachloride, antimony nitrate or bismuth chloride.

La Lande, U.S. Pat. No. 2,395,931, discloses a decolorizing adsorbent or catalyst comprising a water-insoluble metal aluminate formed by the reaction in aqueous solution of an alkali metal aluminate and a water-soluble salt of a metal capable of forming a water-insoluble metal aluminate in the presence of a compound yielding ammonium ions. Suitable water-soluble salts of metals capable of forming a water-insoluble metal aluminate include the chlorides or sulfates of magnesium, calcium, or aluminum, and soluble salts of strontium, barium, lead, copper, cadmium, iron, chromium, cobalt, nickel, manganese, thorium, cerium, beryllium, molybdenum, tin, titanium, zirconium, tungsten and vanadium. The catalyst is disclosed for use in decolorizing hydrocarbon oils.

Mecorney et al., U.S. Pat. No. 2,697,730, disclose a catalyst comprising one or more metals, such as copper, silver, chromium, manganese, nickel, tungsten, cobalt, iron, cadmium, uranium, thorium, tin or zinc, either in the form of the elemental metals, their oxides, hydroxides, or salts, wherein the metal component is supported on activated alumina or diatomaceous earth. The catalyst is disclosed for use in synthesizing higher ketones.

Cislak et al., U.S. Pat. No. 2,744,904, disclose a process for preparing pyridine and 3-picoline by reacting acetylene, ammonia and methanol in the presence of a catalyst comprising activated alumina impregnated with cadmium fluoride.

Finch et al., U.S. Pat. No. 2,763,696, disclose a method for reducing alpha- or beta-olefinic aldehydes or ketones to the corresponding alpha- or beta-unsaturated alcohols by direct hydrogenation of the aldehydes or ketones in the vapor phase and in the presence of a catalyst comprising elemental cadmium, its oxide, or a mixture thereof, and one or more additional metals known to have hydrogenating-dehydrogenating characteristics, such as a heavy metal selected from the first, second, sixth or eighth groups of the Periodic Table of the Elements. These metal components of the catalyst are disclosed as being employed either in the unsupported state or as supported on a suitable carrier, such as silica, alumina, kieselguhr or other diatomaceous earth material, pumice or the like.

Pearson et al., U.S. Pat. No. 3,725,531, disclose a process wherein industrial off-gases containing organic sulfur components are contacted with an alumina base catalyst to convert these organic sulfur components to easily removable compounds, such as carbon dioxide and elemental sulfur. The catalyst employed comprises an alumina base support in combination with at least one metal selected from strontium, calcium, magnesium, zinc, cadmium, barium and molybdenum.

Eurlings et al., U.S. Pat. No. 3,862,055, disclose a method for the preparation of a catalyst system having a catalytically-active component of an oxide, metal or alloy of any one or more of copper, zinc, cadmium, nickel, cobalt, iron, manganese or magnesium, homogeneously dispersed over a solid particulate inorganic thermostable carrier material. Suitable inorganic thermostable materials, for use as the carrier, are disclosed generally as including synthetic or mineral carrier materials, such as alumina or silica.

Eberly, U.S. Pat. No. 4,358,297, discloses a process wherein a particulate sorbent mass of zeolite, which has been ion-exchanged with zinc or cadmium to provide pore size openings of at least about 5 angstroms, is contacted with a moist hydrocarbon process stream which contains sulfur, sulfur compounds, and other contaminants, these being adsorbed onto the particulate sorbent mass.

Mathe et al., U.S. Pat. No. 4,361,500, disclose a process for the preparation of a supported metal catalyst containing at least one metal belonging to Group A and optionally at least one metal belonging to Group B, wherein Group A encompasses palladium, rhodium, ruthenium, platinum, iridium, osmium, silver, gold and cadmium, and Group B encompasses zinc, mercury, germanium, tin, antimony and lead. This patent discloses that any of the known substances commonly used as supports for catalysts can be used as a support in the catalyst disclosed, and the following supports are specifically mentioned: activated carbons, aluminum oxides, silicon dioxides, aluminosilicates and various molecular sieves, and barium sulfate. The catalyst is disclosed for use in hydrogenation reactions.

OBJECTS OF THE INVENTION

It is a general object of the present invention to provide a catalyst for the direct production of gasoline boiling range aliphatic compounds and aromatic compounds from less valuable materials.

More particularly, it is an object of the present invention to provide a catalyst for the direct production in a single step of branched aliphatic hydrocarbons which boil in the gasoline range.

It is another object of the present invention to provide a catalyst for the direct production in a single step of alkylated aromatic compounds.

It is a related object of the present invention to provide a catalyst for the direct production in a single step of gasoline boiling range aliphatic compounds and aromatic compounds from less valuable materials.

Other objects and advantages of the invention will become apparent upon reading the following detailed description and appended claims.

SUMMARY OF THE INVENTION

The present invention is a catalyst composition comprising a cadmium component and a support material comprising at least one of a crystalline borosilicate molecular sieve and a pillared smectite or vermiculite clay, wherein the cadmium component is in the form of the elemental metal, its oxide or salt or a combination thereof, and wherein the cadmium component is present at a concentration level in the range of from about 0.1 to about 20 weight percent, calculated as cadmium oxide and based on the weight of the catalyst.

DETAILED DESCRIPTION

Catalysts of this invention comprise a cadmium component and a support material comprising at least one of crystalline borosilicate molecular sieve and a pillared smectite or vermiculite clay. The cadmium component can be present either as a component deposited on the support or as a component formed from cadmium ions exchanged into the support replacing exchangeable cations in the support. The cadmium component is in the form of elemental cadmium, its oxide or salt or a combination thereof, and is present at a concentration level in the range of from about 0.1 to about 20 weight percent, calculated as cadmium oxide and based on the weight of the catalyst. Preferably the cadmium component is present at a concentration level of from about 1 to about 10 weight percent, calculated as cadmium oxide and based on the weight of the catalyst. The cadmium component is preferably in the form of cadmium oxide.

Crystalline borosilicates are described in U.S. Pat. No. 4,269,813, which patent is specifically incorporated herein by reference. A crystalline borosilicate molecular sieve contains exchangeable cations and can suitably be in the unexchanged or cation-exchanged form. A crystalline borosilicate which is suitable for use in, or as, the support component of the catalyst of this invention is a molecular sieve material having the following composition in terms of mole ratios of oxides:

$$0.9 +/- 0.2 M_{2/n}O:B_2O_3:ySiO_2:zH_2O$$

wherein M is at least one cation having a valence of n, y is within the range of 4 to about 600, and z is within the range of 0 to about 160, and providing an X-ray pattern providing the following X-ray diffraction lines and assigned strengths:

| d Angstroms | Assigned Strength |
| --- | --- |
| 11.2 ± 0.2 | W–VS |
| 10.0 ± 0.2 | W–MS |
| 5.97 ± 0.07 | W–M |
| 3.82 ± 0.05 | VS |
| 3.70 ± 0.05 | MS |
| 3.62 ± 0.05 | M–MS |
| 2.97 ± 0.02 | W–M |
| 1.99 ± 0.02 | VW–M |

M can be a cadmium ion, and thus the cadmium component can be incorporated into the crystalline borosilicate molecular sieve support itself, in addition to or instead of being deposited on the surface of the crystalline borosilicate molecular sieve support.

Suitable methods for preparing the aforesaid crystalline borosilicate molecular sieve are disclosed in Klotz, U.S. Pat. No. 4,269,813 and in Haddid, European Patent Application No. 82303246.1 which was published on Jan. 5, 1983.

Pillared smectite and vermiculite clays, which are also suitable for use in, or as, the support component of the catalyst of this invention, are often referred in the literature as pillared interlayered clays and occasionally as molecular sieves. The smectite clays comprise montmorillonite, beidellite, montronite, volchonskoite, hectorite, saponite, stevensite, sauconite and pimelite. Some pillared smectite and vermiculite clay materials that are suitable for use in the support of the catalyst of this invention, and methods for preparing such clays, are disclosed in Vaughan et al., U.S. Pat. No. 4,176,090; Shabria et al., U.S. Pat. No. 4,216,188; Shabtai, U.S. Pat. No. 4,238,364; D'Aniello, U.S. Pat. No. 4,380,510; Pinnavaia, "Intercalated Clay Catalysts," *Science*, Vol. 220, pages 365–371 (Apr. 22, 1983) and Vaughan et al., "Preparation of Molecular Sieves Based on Pillared Interlayered Clays (PILC)," *Fifth International Conference on Zeolites, pages* 94–101 and in the references cited therein. Preferably, a suitable pillared smectite clay comprises a multiplicity of cations interposed between the molecular layers of the clay and maintaining the spacing between the molecular layers in the range of from about 6 angstroms to about 10 angstroms at a temperature of at least 300° C. in an air atmosphere for at least 2 hours.

Preferably, the support comprises a combination of an aforesaid molecular sieve material or an aforesaid pillared smectite or vermiculite clay material with an amorphous refractory inorganic oxide, such as alumina, zirconia, titania, an oxide of a metal of the lanthanide series, an oxide of a metal of the actinide series, a combination thereof, or a combination thereof with silica or magnesia. The amorphous refractory inorganic oxide can also include adjuvants, such as one or more oxides of phosphorus or boron, or a halogen, such as chlorine or fluorine. In such cases, the concentrations of the amorphous inorganic oxide and of the crystalline borosilicate molecular sieve material and/or pillared smectite or vermiculite clay material are not critical. Preferably, the amorphous refractory inorganic oxide content is at least high enough to be effective to give the support sufficient strength and integrity so that the ultimate catalyst composition can be employed without appreciable damage to the catalyst. In such case, the total concentration of the crystalline borosilicate molecular sieve material and/or pillared smectite or vermiculite clay material in such mixture is preferably from 5 to 90 weight percent, more preferably from 20 to 60 weight percent, based on the weight of the support, which support is made up of the amorphous refractory inorganic oxide and the crystalline borosilicate molecular sieve material and/or the pillared smectite or vermiculite clay material.

Preferably, when the support comprises a mixture of a crystalline borosilicate molecular sieve and/or pillared smectite or vermiculite clay and an amorphous refractory inorganic oxide, the support is in the form of a dispersion of the crystalline borosilicate molecular sieve component and/or pillared smectite or vermiculite clay component in a matrix of the amorphous refractory inorganic oxide. Such dispersions can be prepared by well-known techniques, such as blending the crystalline borosilicate molecular sieve component and/or pillared smectite or vermiculite clay component, preferably in finely-divided form, into a sol, hydrosol or hydrogel of the inorganic oxide, and then adding a gelling medium, such as ammonium hydroxide, and stirring to produce a gel. Alternately, the crystalline borosilicate molecular sieve component and/or pillared smectite or vermiculite clay component is blended into a slurry of the amorphous inorganic oxide. In either case, the resulting mixture can be dried, shaped, if desired, and then calcined to form the final support component. A less preferred, but still suitable, method for preparing a suitable dispersion of the crystalline borosilicate molecular sieve component and/or pillared smectite or vermiculite clay component in the inorganic oxide is to dry-blend particles of each, preferably in finely-divided form, and then to conduct any desired shaping operations, such as pelletizing or extrusion; the resulting mixture is then calcined.

The catalysts of this invention can be prepared by impregnation of an aforesaid suitable support with at least one precursor of the cadmium component. Any convenient conventional impregnation technique can be employed for this purpose. For example, when the support comprises both an amorphous refractory inorganic oxide and a crystalline borosilicate molecular sieve and/or a pillared smectite or vermiculite clay, numerous convenient impregnation techniques can also be employed. For example, finely-divided crystalline borosilicate molecular sieve material and/or pillared smectite of vermiculite clay material can be stirred into a sol or gel of a refractory inorganic oxide, and at least one soluble compound of cadmium is added to the sol or gel, followed by co-gelling of the sol or gel mixture by the addition of dilute ammonia. The resulting co-gelled material is then dried and calcined.

In another method of preparation, finely-divided crystalline borosilicate molecular sieve material and/or pillared smectite of vermiculite clay material are mixed into a sol or gel of a refractory inorganic oxide; the sol or gel mixture is co-gelled by the addition of dilute ammonia and the resulting gel is subsequently dried, calcined, cooled, and then impregnated with a solution or solutions of at least one soluble compound of cadmium. As an alternate method of preparation, a hydrogel of a refractory inorganic oxide is blended with finely-divided crystalline borosilicate molecular sieve material and/or pillared smectite or vermiculite clay, and a solution or solutions of at least one soluble compound of cadmium is added to this blend, and the resulting mixture is thoroughly blended. The blended mixture is then dried and calcined.

In still another method of preparation, the crystalline borosilicate molecular sieve material and/or pillared smectite or vermiculite clay material can be pulverized into a finely-divided state and then physically admixed with a finely-divided powder of the selected refractory inorganic oxide component. After a thorough blending of the solid components, the resulting mixture can be co-pelleted, and impregnated with one or more solutions of a cadmium compound.

It is, of course, also suitable to impregnate only one of the amorphous refractory inorganic oxide, the crystalline borosilicate molecular sieve material or pillared smectite or vermiculite clay material in the mixture, or to impregnate each of the aforesaid amorphous inorganic oxide, crystalline borosilicate molecular sieve material and/or pillared smectite or vermiculite clay material separately, and then to blend the inorganic oxide and crystalline borosilicate molecular sieve material and/or pillared smectite or vermiculite clay material. Thus, it is contemplated that, if the catalyst of this invention comprises an amorphous refractory inorganic oxide and at least one of a crystalline borosilicate molecular sieve material and a pillared smectite or vermiculite clay material, the cadmium component can be deposited on only one, only two, or all of the components of the support.

It is preferred that the impregnation of the crystalline borosilicate molecular sieve component and pillared smectite or vermiculite clay component is conducted at a pH of at least about 2 in order to avoid substantial destruction of the crystallinity of the aforesaid support component. More preferably, the pH of the impregnating solution(s) in such case is from about 2.5 to about 6 in order to ensure substantial retention of the crystallinity of the aforesaid support component. Of course, the optimum pH range(s) of the impregnating solution(s) varies somewhat depending on the specific crystalline borosilicate molecular sieve component and pillared smectite or vermiculite clay component employed in the preparation of a given catalyst.

In each of the above preparations involving a crystalline borosilicate molecular sieve material, the crystalline borosilicate molecular sieve material employed can be either in its unexchanged form or in its ion-exchanged form. Preferably, the crystalline borosilicate molecular sieve material is one which has previously been cation-exchanged. A suitable cation-exchange procedure comprises making a slurry of the crystalline borosilicate molecular sieve material in a solution of a cation, such as ammonium ions, which is to be exchanged with the alkali metal in the molecular sieve material, stirring the slurry at a temperature of about 100° C., for at least about 2 hours to about one week, filtering the slurry, washing the filtered solid with distilled water, and drying and calcining the solid.

It is also suitable to incorporate the precursor of the cadmium component into the crystalline borosilicate molecular sieve by cation exchange using a convenient, conventional ion exchange procedure, such as the one described generally hereinabove. Thus, the cadmium component can be incorporated into the crystalline borosilicate molecular sieve support itself, in addition to or instead of being deposited on the surface of the crystalline borosilicate molecular sieve support.

Suitable conditions for drying the above-described cadmium-impregnated or cadmium-exchanged supports comprise a temperature in the range of from about 90° C. to about 200° C. and a drying time of from about 0.5 to about 30 hours. Suitable calcination conditions in such methods comprise a temperature in the range of about 480° C. to about 760° C. and a calcination time of from about 2 to about 5 hours. Preferred drying and calcination conditions are a temperature of about 120° C. for about 1-2 hours and a temperature of about 538° C. for about 1-2 hours, respectively.

The catalyst of this invention can be employed to catalyst the general method comprising reacting hydrogen with a material selected from the group consisting of (a) carbon monoxide, (b) at least one of an alcohol containing from 1 to 6 carbon atoms and an olefin containing from 2-6 carbon atoms, and (c) a mixture of an aromatic compound and at least one of carbon monoxide and an alcohol containing from 1 to 6 carbon atoms, in the presence of an aforesaid catalyst suitable for use in the method of this invention. The conditions employed in this general method include a temperature in the range of from about 300° C. to about 480° C. and a pressure in the range of from about 5 to about 150 kilograms per square centimeter.

For the reaction between carbon monoxide and hydrogen, the mole ratio of carbon monoxide-to-hydrogen is in the range of from about 1:10 to about 10:1, preferably from about 2:1 to about 1:4. In such cases, it is also preferred that the reaction is performed at a temperature in the range of from about 315° C. to about 425° C., at a pressure of at least 35 kilograms per square centimeter, and with a space velocity of from about 0.2 to about 5 moles of carbon monoxide per gram of catalyst per hour.

For the reaction between hydrogen and at least one of the aforesaid alcohol and the aforesaid olefin the alcohol preferably comprises methanol, ethanol, propanol or a combination thereof. When an alcohol is not a reactant, the olefin preferably comprises propylene, butylene, amylene or a combination thereof. When an alcohol is a reactant, the olefin comprises ethylene, propylene, butylene or a combination thereof. If an alcohol is a reactant, the mole ratio of alcohol-to-hydrogen is from about 1:10 to about 10:1, preferably from about 4:1 to about 1:4. If an olefin is a reactant, the mole ratio of olefin-to-hydrogen is from about 10:1 to about 1:10, preferably from about 4:1 to about 1:1. If both an alcohol and an olefin are reactants, the mole ratio of alcohol-to-olefin is from about 10:1 to about 1:10, preferably from about 3:1 to about 1:3. In such cases, it is also preferred that the reaction is performed at a temperature in the range of from about 315° C. to about about 425° C., at a pressure of at least about 10 kilograms per square centimeter, and with a space velocity of from about 0.01 to about 0.1 moles of each of the alcohol and olefin that is present per gram of catalyst per hour.

For the reaction between an aromatic compound, hydrogen and at least one of carbon monoxide and an alcohol containing from 1 to 6 carbon atoms, the aromatic compound is preferably an unsubstituted or alkylated benzene or naphthalene. The alcohol preferably comprises methanol, ethanol, propanol or a combination thereof. The mole ratio of carbon monoxide or alcohol or both-to-hydrogen is in the range of from about 1:10 to about 10:1, preferably from about 4:1 to about 1:4; and the mole ratio of carbon monoxide or alcohol or both-to-aromatic compound is from about 10:1 to about 1:10, preferably from about 2:1 to about 1:10. Preferably, the space velocity of the aromatic compound is from about 0.02 to about 0.5 moles of the aromatic compound per gram of catalyst per hour. It is also preferred that the reaction between the aromatic compound, hydrogen and at least one of carbon monoxide and an alcohol containing from 1 to 6 carbon atoms is performed at a temperature in the range of from about 315° C. to about 450° C., at a pressure in the range of from about 30 to about 100 kilograms per square centimeter.

The present invention will be more clearly understood from the following specific examples.

EXAMPLE 1

180 grams of crystalline borosilicate (obtained from Amoco Chemicals Corporation and designated HAMS-1B) was suspended in sufficient water to form a sauce-like consistency and combined and blended with 3600 grams of an alumina sol containing about 10 weight percent of alumina. 400 milliliters of an aqueous solution containing about 50 weight percent of ammonium hydroxide was added to the blend to gel the mixture of crystalline borosilicate and alumina. The resulting gel was dried at 120° C. in air overnight. The dried particles were ground to pass a 100 mesh sieve (U.S. Series), mulled with water, extruded to a diameter of 0.32 centimeter, dried at 120° C. overnight and calcined at 540° C. in air overnight. The resulting composition contained 40 weight percent of crystalline borosilicate HAMS-1B and 60 weight percent of alumina.

A solution containing 3 grams of $Cd(NO_3)_2.4H_2O$ in 8 milliliters of water was combined and blended for 1 hour with 19 grams of the aforesaid composition containing 40 weight percent of HAMS-1B. The blend was then dried at 120° C. for 1 hour and calcined at 540° C. in air for 1 hour. The resulting catalyst contained 5 weight percent of cadmium oxide, based on the weight of the catalyst.

EXAMPLE 2

A suspension of 400 grams of a bentonite, 90 weight percent of which is montmorillonite (supplied by American Colloid Company and designated Volclay 325), in 227 cubic centimeters of water was mixed with 304 grams of a 50 weight percent solution of Reheis alumina Chlorhydrol, and the pH of the resulting suspension was adjusted to 4 with ammonium hydroxide. The suspension was heated at 72° C. for 1 hour and then filtered, and the resulting separated solid was washed with water, dried at 100° C. and calcined at 500° C. for 2 hours. The resulting alumina-expanded smectite clay had a d-spacing of 16.6 angstroms as measured by X-ray diffraction. The spacing between the molecular layers of the montmorillonite was between 6 and 10 angstroms and was stable at a temperature of at least 300° C. in an air atmosphere for at least 2 hours.

30.27 grams of this composition was combined with 221.5 grams of an alumina sol containing about 9 weight percent of alumina, and 10 grams of an aqueous solution containing about 28 weight percent of ammonium hydroxide was added to gel the resulting mixture. The resulting gel was dried at 120° C. and calcined at 540° C., for 6 hours. The resulting composition contained 60 weight percent of the alumina-expanded smectite clay and 40 weight percent of alumina.

A solution containing 2.4 grams of $Cd(NO_3)_2.4H_2O$ in 8 milliliters of water was combined and blended with 19 grams of the aforesaid composition containing 60 weight percent of the alumina-expanded smectite clay and 40 weight percent of alumina. The blend was then dried at 120° C. and calcined at 540° C. for 4 hours. The resulting catalyst contained 5 weight percent of cadmium oxide, based on the weight of the catalyst.

EXAMPLE 3

The procedure of Example 2 was repeated except that a solution containing 5.41 grams of $Cd(NO_3)_2.4H_2O$ in 9 grams of water was combined and blended with 22.75 grams of the composition containing 60 weight percent of the alumina-expanded smectite clay and 40 weight percent of alumina. The blend was then dried at 120° C. and calcined at 540° C. for 4 hours. The resulting catalyst contained 9 weight percent of cadmium oxide, based on the weight of the catalyst.

EXAMPLES 4–10

Examples 4–10 were performed using a 300-cubic centimeter, back-mixed reactor in which the flow into the reactor of each gaseous and liquid reactant employed was controlled individually. To start a run in each of Examples 4–10, 10 grams of the particular catalyst used was loaded into the reactor, and the reactor was closed. The pressure of the reactor was then raised to the desired level by introducing the gaseous reactant(s) employed. The temperature of the reactor was then raised to the desired level, at which point any liquid reactant(s) employed was then introduced into the reactor where it contacted the catalyst and gaseous reactant(s). Products and unreacted reactants passed continuously out of the reactor.

The catalyst, temperature, pressure and feed rates of each reactant employed in Examples 4–10 are presented in Tables 1–2. The feed rate of each liquid reactant is presented in Tables 1–2 in terms of its liquid hourly space velocity—that is, the feed rate of the liquid in cubic centimeters per hour divided by the number (10) of grams of catalyst in the reactor. The combined feed rate of the gaseous reactant(s) is presented in Tables 1–2 in terms of the gas weight hourly space velocity—that is, the combined gaseous feed rate in cubic centimeters per hour divided by weight of catalyst in the reactor. When both carbon monoxide and hydrogen were employed, they were introduced into the reactor at a mole ratio of carbon monoxide-to-hydrogen of 1:2. A mixture of hydrogen and carbon monoxide was employed in Examples 4, 9 and 10. Hydrogen was the only gas employed in Examples 5–8. Methanol was the liquid feed in Examples 5–7. Propylene is the liquid feed in Example 8. Benzene was the aromatic feed in Examples 9 and 10.

The compositions of the organic products for each of Examples 4–10 are also indicated in Tables 1–2. In Table 1, the concentrations of butylenes are not reported separately but are included in the concentrations of $i-C_5H_{12}$ and $n-C_5H_{12}$.

TABLE 1

| | Example No. | | | | |
|---|---|---|---|---|---|
| | 4 | 5 | 6 | 7 | 8 |
| Catalyst from Example No. | 2 | 2 | 2 | 2 | 3 |
| Temperature (°C.) | 399 | 405 | 432 | 427 | 399 |
| Pressure (atm.) | 34 | 34 | 34 | 34 | 34 |

TABLE 1-continued

|  | Example No. | | | | |
| --- | --- | --- | --- | --- | --- |
|  | 4 | 5 | 6 | 7 | 8 |
| Gas feed rate (cc./hr./gm.) | 2000 | 1800 | 2250 | 4500 | 1050 |
| Liquid feed rate (cc./hr./gm.) | — | 1.0 | 1.0 | 3.0 | 1.0 |
| Product Composition (Wt. %) | | | | | |
| $CH_4$ | 28 | 11 | 18 | 13 | 1 |
| $C_2H_6$—$C_2H_4$ | 7 | 5 | 7 | 5 | — |
| $C_3H_8$ | 11 | 10 | 8 | 2 | 30 |
| $C_3H_6$ | 1 | 2 | 4 | 5 | — |
| i-$C_4H_{10}$ | 19 | 27 | 20 | 9 | 13 |
| n-$C_4H_{10}$ | 4 | 5 | 4 | 2 | — |
| i-$C_5H_{12}$ | 9 | 14 | 12 | 6 | 14 |
| n-$C_5H_{12}$ | 1 | 1 | 1 | 1 | — |
| i-$C_6H_{14}$ | 5 | 8 | 8 | 6 | 27 |
| n-$C_6H_{14}$ | 1 | 0 | 0 | 0 | — |
| $C_6+$ | 14 | 15 | 15 | 14 | 13 |
| DME | — | 2 | 3 | 36 | — |

TABLE 2

|  | Example No. | |
| --- | --- | --- |
|  | 9 | 10 |
| Catalyst from Example No. | 1 | 1 |
| Temperature (°C.) | 399 | 421 |
| Pressure (atm.) | 34 | 34 |
| Gas feed rate (cc./hr./gm.) | 1550 | 1550 |
| Liquid feed rate (cc./hr./gm.) | 1.0[1] | 1.0[1] |
| Aromatic conversion (%) | 24 | 29 |
| Product Composition (Wt. %) | | |
| $C_1$-$C_6$ | 5 | 5 |
| Benzene | — | — |
| Toluene | 65 | 47 |
| Ethylbenzene | 2 | 2 |
| m/p-xylene | 14 | 24 |
| o-xylene | — | — |
| 1,3,5-trimethylbenzene | — | — |
| pseudocumene | 3 | 9 |
| 1,2,3-trimethylbenzene | 1 | — |
| tetramethylbenzene | 3 | 1 |
| Other aromatics | — | 14 |

Footnotes
[1]Benzene

Example 4 involves the reaction between carbon monoxide and hydrogen. The results of this example illustrate both a high selectivity for the production of branched hydrocarbons in this reaction relative to the production of unbranched hydrocarbons having the same number of carbon atoms, and the production of $C_6+$, which is primarily a mixture of branched hydrocarbons containing at least 7 carbon atoms.

Examples 5–8 involve reactions between hydrogen and at least one of an alcohol containing from 1 to 6 carbon atoms and an olefin containing from 2 to 6 carbon atoms. Comparison of the results of Example 5 with the results of Example 4 illustrates that relatively smaller amounts of methane and relatively greater amounts of $C_6+$ are produced in the reaction between hydrogen and the alcohol and/or olefin than in the reaction between hydrogen and carbon monoxide.

Comparison of the results of Examples 5 and 6 illustrates that increases in the reaction temperature result in increases in the relative yield of methane and in decreases in the relative yields of branched hydrocarbons.

Examples 9 and 10 involve the reaction between an aromatic compound, hydrogen and at least one of carbon monoxide and an alcohol containing from 1 to 6 carbon atoms. In both cases, products that are methylated derivatives—other than disproportionation products—of the aromatic component of the feed were formed. Examples 9 and 10 illustrate that increases in reaction temperature afford increased conversion of the aromatic feed component, and increased overall yields of polymethylated products, such as pseudocumene, tetramethylbenzenes and other aromatics.

From the above description, it is apparent that the objects of the present invention have been achieved. While only certain have been set forth, alternative embodiments and various modifications will be apparent from the above description to those skilled in the art. These and other alternatives are considered equivalents and within the spirit and scope of the present invention.

Having described the invention, what is claimed is:

1. A catalyst composition comprising a cadmium component and a support material comprising at least one of a crystalline borosilicate molecular sieve and a pillared smectite or vermiculite clay, wherein the cadmium component is in the form of the elemental metal, its oxide or salt or a combination thereof, and wherein the cadmium component is present at a concentration level in the range of from about 0.1 to about 20 weight percent, calculated as cadmium oxide and based on the weight of the catalyst.

2. The catalyst composition of claim 1 wherein the cadmium component is in the form of cadmium oxide.

3. The catalyst composition of claim 1 wherein the cadmium component is present at a concentration level in the range of from about 1 to about 10 weight percent, calculated as cadmium oxide and based on the weight of the catalyst.

4. The catalyst composition of claim 1 wherein the crystalline borosilicate molecular sieve comprises a molecular sieve material having the following composition in terms of mole ratios of oxides:

$$0.9\pm0.2M_{2/n}O:B_2O_3:ySiO_2:zH_2O$$

wherein M is at least one cation having a valence of n, y is between 4 and about 600, and z is between 0 and about 160, and providing an X-ray diffraction pattern comprising the following X-ray diffraction lines and assigned strengths:

| ~d (Å) | Assigned Strength |
| --- | --- |
| 11.2 ± 0.2 | W–VS |
| 10.0 ± 0.2 | W–MS |
| 5.97 ± 0.07 | W–M |
| 3.82 ± 0.05 | VS |
| 3.70 ± 0.05 | MS |
| 3.62 ± 0.05 | M–MS |
| 2.97 ± 0.02 | W–M |
| 1.99 ± 0.02 | VW–M |

5. The catalyst composition of claim 1 wherein the pillared smectite or vermiculite clay comprises a multiplicity of cations interposed between the molecular layers of the clay and maintaining the spacing between the molecular layers in the range of from about 6 angstroms to about 10 angstroms at a temperature of at least 300° C. in an air atmosphere for at least 2 hours.

6. The catalyst composition of claim 1 wherein the support comprises from about 20 to about 95 weight percent of an amorphous refractory inorganic oxide and from about 5 to about 80 weight percent of the crystalline borosilicate molecular sieve or pillared smectite or vermiculite clay.

7. The catalyst composition of claim 6 wherein the refractory inorganic oxide comprises alumina, zirconia, titania, an oxide of a metal of the lanthanide series, an oxide of a metal of the actinide series, a combination thereof, or a combination thereof with silica or magnesia.

* * * * *

UNITED STATES PATENT OFFICE
CERTIFICATE OF CORRECTION

Patent No. 4,507,399　　　　　　　　　Dated March 26, 1985

Inventor(s) JEFFREY T. MILLER - THOMAS D. NEVITT

It is certified that error appears in the above-identified patent and that said Letters Patent are hereby corrected as shown below:

| Col. | Line | | | |
|------|------|------|-----------|--------|
| 6 | 51 | "of" | should be | -- or -- |
| 6 | 59 | "of" | should be | -- or -- |

Signed and Sealed this

Twentieth Day of August 1985

[SEAL]

Attest:

DONALD J. QUIGG

Attesting Officer　　Acting Commissioner of Patents and Trademarks